United States Patent [19]

Corliss

[11] Plant 4,795

[45] Nov. 24, 1981

[54] EUONYMUS PLANT—CORLUTZ VARIETY

[75] Inventor: Clifford D. Corliss, Ipswich, Mass.

[73] Assignee: The Conard-Pyle Comany, West Grove, Pa.

[21] Appl. No.: 151,247

[22] Filed: May 19, 1980

[51] Int. Cl.[3] ..... A01H 5/12

[52] U.S. Cl. ..... Plt./63

[58] Field of Search ..... Plt./63

*Primary Examiner*—Robert E. Bagwill

*Attorney, Agent, or Firm*—Burns, Doane, Swecker & Mathis

[57] ABSTRACT

A new and distinct variety of *Euonymus fortunei* which is a branch mutation of the Emerald'N Gold variety (i.e. U.S. Plant Pat. No. 2,231) is provided. The new variety possesses larger leaves than the parent variety which are of a richer attractively variegated coloration. More specifically, the mature leaves are dark green and have light to medium yellow margins. The new variety has a more upright growth habit than the parent variety and forms a larger plant. Unlike the parent there is no substantial change in the leaf coloration and leaf orientation during the winter.

2 Drawing Figures

SUMMARY OF THE INVENTION

The new variety was discovered and selected by me during 1969 while present in a cultivated block of plants of the Emerald'N Gold variety (U.S. Plant Pat. No. 2,231) of *Euonymus fortunei* being grown under my direction at the nursery property of Corliss Bros., Inc. at Ipswich, Mass. A distinctive branch of a single plant was discovered having a growth habit, leaf size, and leaf appearance which differed from that of the Emerald'N Gold variety. This branch was preserved and continued close observation has confirmed its distinctive characteristics which differ from all varieties of *Euonymus fortunei* of which I am aware.

The following combination of characteristics is exhibited by the new variety:

(a) a more upright habit of growth which yields a larger plant than the parent variety, (b) large richly colored variegated leaves which when mature are dark green with light to medium yellow margins, (c) the propensity of exhibiting no substantial change in leaf coloration during winter, (d) a propensity to resist a change in leaf orientation during winter (i.e. to a position generally parallel to the stem), (e) vigorous growth characteristics, (f) the ability to thrive under a wide range of climatic conditions, and (g) the ability to be sheared within prescribed limits or shaped to a specific form.

Asexual reproduction of my new variety by cuttings has been accomplished at Ipswich, Mass. and West Grove, Pa. Such propagation through at least six generations has demonstrated that the unique combination of characteristics has been established and is transmitted to successive generations.

The new variety has been named the Corlutz variety.

BRIEF DESCRIPTION OF THE PHOTOGRAPHS

The accompanying photographs show a typical specimen of the variety as depicted in color as true as reasonably possible to make the same in a color illustration of this character. The photographs were made during mid-summer of a representative plant and plant parts thereof two growing seasons following the year of propagation. The subject plant was grown at West Grove, Pa. in an artificial soilless medium.

FIG. 1 illustrates the appearance of a representative plant of the new variety, and FIG. 2 illustrates representative branches of the new variety as well as the appearance of the upper and under surfaces of typical leaves.

DETAILED DESCRIPTION

Figure 1:
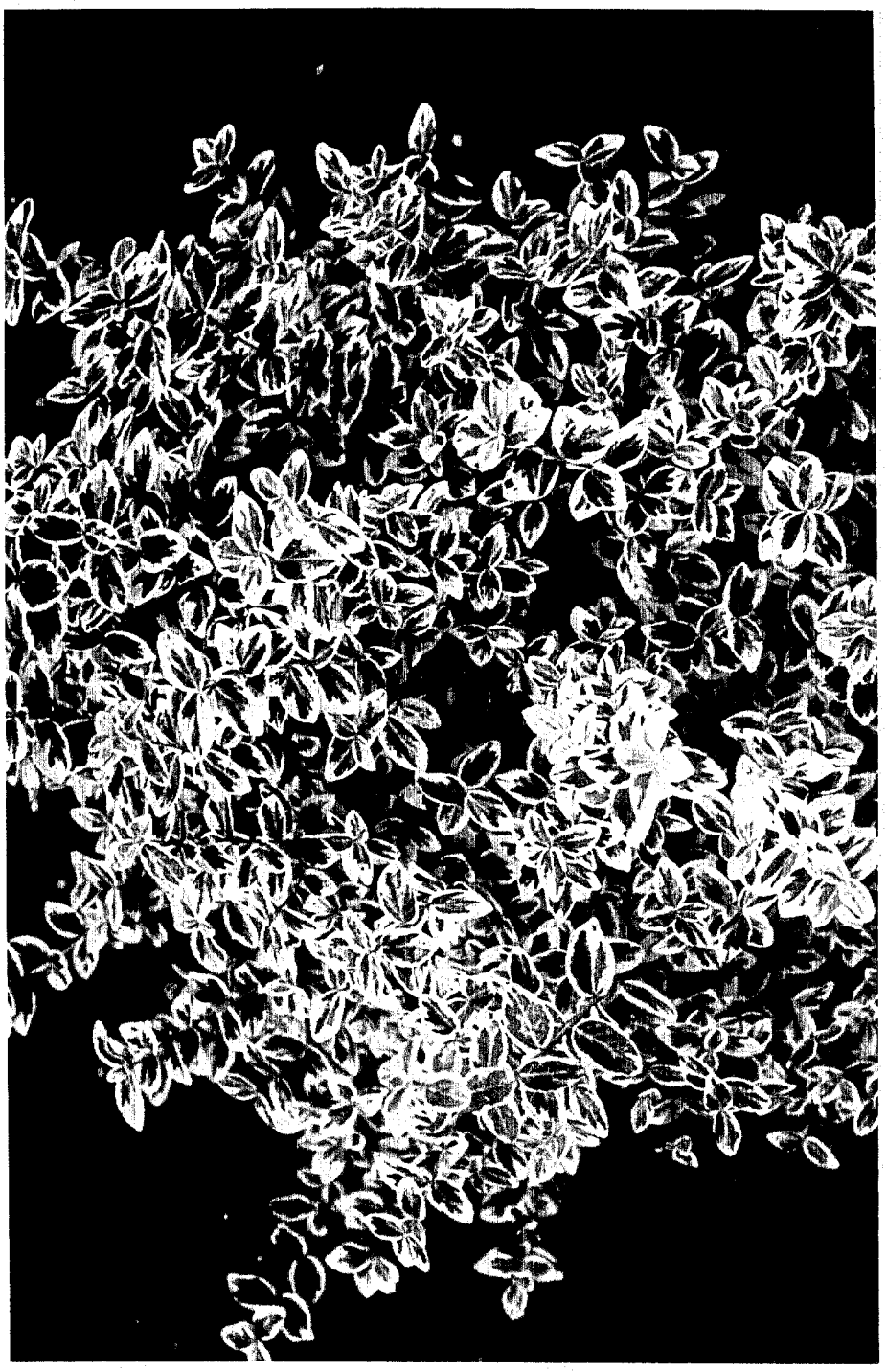
Figure 2:
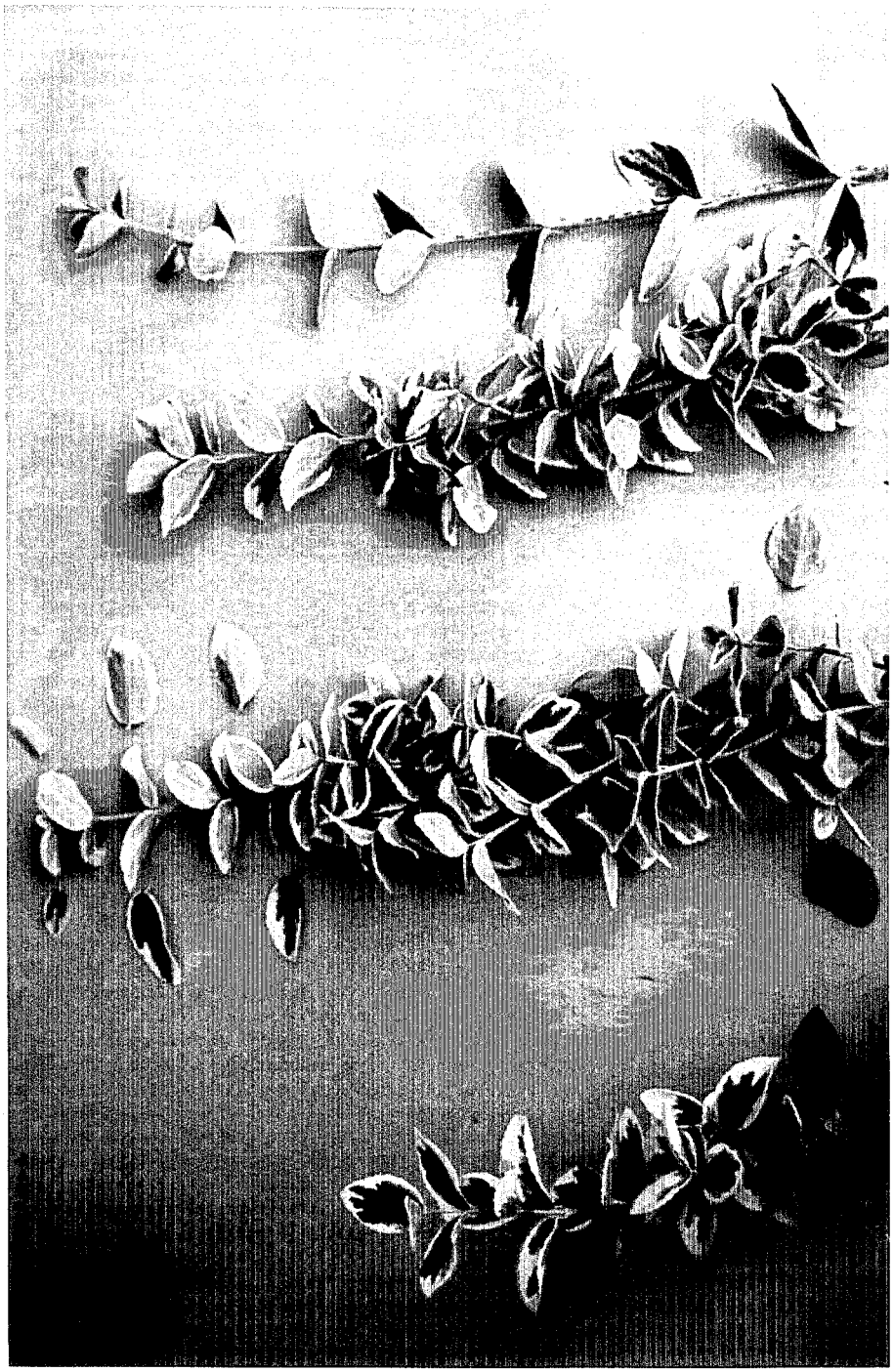

The following is a detailed description of my new variety, with color terminology in accordance with the R.H.S. Colour Chart of the Royal Horticultural Society, London, England. The description was made during mid-summer following the observation of representative plants two growing seasons following the year of propagation which were grown in an artificial soilless medium at West Grove, Pa.

Growth habit: More upright than parent variety, yielding a larger plant. The plants described above commonly possess a height of 24 to 28 inches and a breadth of 21 to 24 inches while the Emerald'N Gold variety commonly possesses a height of 18 to 21 inches and a breadth of 15 to 18 inches under the same growing conditions. The plant is suitable for growing as an attractive ornamental.

Foliage:

*Type.*—Broadleaf evergreen; petioled; opposite.

*Shape.*—Slightly variable in shape. Mostly ovate with some eliptic. Base obtuse. Margins serrate to serrate-crenate.

*Petioles.*—Approximately 3 to 5 mm. in length.

*Size.*—Mature leaves on current year's growth are larger than those of the Emerald'N Gold variety. More specifically, the leaves of the present variety under the above growing conditions commonly measure approximately 2.1 to 3.7 cm. in length and 1.5 to 2.4 cm. in breadth, while those of the Emerald'N Gold variety commonly measure approximately 1.9 to 3.2 cm. in length and 1.3 to 2.0 cm. in breadth.

*Color—upper surface.*—Immature leaves Green Group 143A edged with irregular band of Yellow-Green Group 151A to 151C, and mature leaves Green Group 137A to 137B edged with irregular band of Light Yellow Group 8B or Yellow Group 13B.

*Color—under surface.*—Duller with less color differentiation than upper surface, commonly Green Group 137C.

In addition to above there commonly is found on well established plants, and occasionally on young plants, random shoots with solid green leaves having a color generally corresponding to that of the Emerald Pride variety (U.S. Plant Pat. No. 1,073), and random shoots with green leaves edged with cream generally corresponding in color to that of the Emerald Gaiety variety (U.S. Plant Pat. No. 1,960).

Flowers: Inconspicuous, infrequently observed.

Hardiness: Good winter hardiness. The new variety has withstood temperatures of −20° F. when grown at Ipswich, Mass.

Disease and drought resistance: Good.

I claim:

1. A new and distinct variety of *Euonymus fortunei* which is a branch mutation of Emerald'N Gold variety, substantially as herein shown and described, characterized particularly as to novelty by the unique combination of:

(a) a more upright habit of growth which yields a larger plant than the parent variety, (b) large richly colored variegated leaves which when mature are dark green with light to medium yellow margins, (c) the propensity of exhibiting no substantial change in leaf coloration during winter, (d) a propensity to resist a change in leaf orientation during winter, (e) vigorous growth characteristics, (f) the ability to thrive under a wide range of climatic conditions, and (g) the ability to be sheared within prescribed limits or shaped to a specific form.

* * * * *